United States Patent [19]

Meurs et al.

[11] Patent Number: 4,663,487
[45] Date of Patent: May 5, 1987

[54] PREPARATION OF 4,4-DISUBSTITUTED CYCLOHEXADIENONES

[75] Inventors: Jan H. H. Meurs; David W. Sopher, both of Amsterdam, Netherlands

[73] Assignee: Shell Oil Company, Houston, Tex.

[21] Appl. No.: 818,640

[22] Filed: Jan. 14, 1986

[30] Foreign Application Priority Data

Jan. 25, 1985 [GB] United Kingdom ............. 8501917

[51] Int. Cl.$^4$ ............................................. C07C 45/29
[52] U.S. Cl. ................................... 568/362; 568/354; 564/462; 558/431
[58] Field of Search ................. 568/362, 361, 354; 564/462, 450, 562; 260/465 E, 465 F, 396 R; 558/431

[56] References Cited

U.S. PATENT DOCUMENTS 2,903,487  9/1959  Coffield ............................. 568/362
3,928,453  12/1975 Atkinson ........................... 568/362
4,051,168  9/1977  Feiring ............................. 568/316
4,477,682  10/1984 Tomita et al. ..................... 568/362
4,560,801  12/1985 Constantini et al. ............. 568/362
4,565,895  1/1986  Constantini et al. ............. 568/362

OTHER PUBLICATIONS

Aropov et al, J. Org. Chem., USSR, vol. 19, pp. 997–998 (1983).
Zarubin et al, J. Org. Chem., USSR, vol. 11, pp. 1269–1274 (1974).
Milaev et al, J. Org. Chem., USSR, vol. 51, pp. 2343–2347 (1981).
Kobrina et al, Chem. Abst., vol. 87, #151814 (1977).
Detsina et al, Chem. Abst., vol. 76, #99261 (1972).

Primary Examiner—James H. Reamer
Attorney, Agent, or Firm—Ronald R. Reper

[57] ABSTRACT

The invention provides a process for the preparation of 4,4-disubstituted cyclohexadienones of which at least one of the substituents is fluorine, which comprises reacting a compound of formula

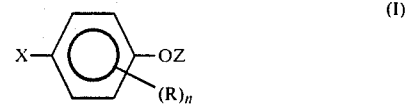

(I)

wheren X represents a hydrogen or halogen atom or an alkyl group, each R independently represents a halogen atom or an alkyl, alkoxy, or cyano or optionally substituted amino group, Z represents a hydrogen atom or an alkyl, acyl or aryloxycarbonyl group, and n is 0 to 4, with hydrogen fluoride and a Pb(IV) compound, in the presence of a compound which acts as a base towards HF.

9 Claims, No Drawings

PREPARATION OF 4,4-DISUBSTITUTED CYCLOHEXADIENONES

BACKGROUND OF THE INVENTION

The present invention relates to a process for the preparation of 4,4-disubstituted cyclohexadienones of which at least one of the 4-substituents is fluorine, and to the 4,4-disubstituted cyclohexadienones thus prepared.

A process for the preparation of an unsubstituted 4,4-difluorocyclohexadienone is known from I. Ya. Aliev, I. N. Rozhkov and I. L. Knunyants, *Izu. Akad. Nauk SSSR, Ser. Khim*, 6 (June 1973) 1430. It describes the anodic oxidations of p-fluoroanisole and p-fluorophenetole on Pt in a solution of $(C_2H_5)_4$ NF.3HF in $CH_3CN$. The starting materials are already fluorinated, so the scope of the reaction is limited to production of 4,4-difluorocyclohexadienone. Furthermore, electrochemical synthesis are not always very practical on an industrial scale.

SUMMARY OF THE INVENTION

According to the invention there is provided a process for the preparation of 4,4-disubstituted cyclohexadienones of which at least one of the substituents is fluorine, which process comprised reacting a compound of formula

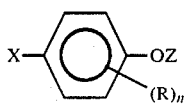

(I)

wherein X represents a hydrogen or halogen atom or an alkyl group, each R independently represents a halogen atom or an alkyl, alkoxy, cyano or optionally substituted amino group, Z represents a hydrogen atom or an alkyl, acyl or aryloxycarbonyl group, and n is 0 to 4, with hydrogen fluoride and a Pb(IV) compound, in the presence of a compound which acts as a base towards HF.

DESCRIPTION OF PREFERRED EMBODIMENTS

In the starting material of formula I, X preferably represents hydrogen, chlorine or methyl. When X in said starting material represents hydrogen or fluorine, the 4,4-disubstituted dione product is a 4,4-difluorocyclohexadienone. However, when X represents another halogen atom or an alkyl group, this atom or group is retained in the reaction product, thus yielding a 4-fluoro-4-X-cyclohexadienone.

The compounds thus prepared therefore may be represented by formula II

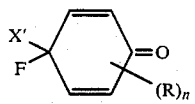

(II)

in which R and n have the same meaning as in the starting compound of formula I, and X' has the same meaning as X, expect when X represents hydrogen, in which case X' stands for fluorine.

Wherever in this application mention is made of alkyl groups, they are preferably $C_{1-5}$ alkyl groups and in particular methyl or ethyl. Thus, groups which contain alkyl groups, such as acyl groups, preferably contain $C_{1-5}$ alkyl groups (the acyl group thus preferably containing 2 to 6 carbon atoms). Although a halogen atom may be a fluorine, chlorine, bromine or iodine atom, fluorine and chlorine are preferred. Optional substituents on an amino group may be for example one or two alkyl moieties.

The optional nuclear substituent or substituents R thus preferably is or are chlorine or fluorine, $C_{1-5}$ alkyl or alkoxy, amino, $C_{1-5}$ alkylamino or di-($C_{1-5}$ alkyl) amino or mixtures thereof. In particular R preferably represents chlorine or methyl. Preferably n is 0 or 1, most preferably 0.

The group —OZ may be an —OH group (the compound of formula I being a phenol), an alkoxy group (the compound formula I being a phenol ether), an acyloxy group (a phenol ester), or an aryloxycarbonyloxy group (a phenyl aryl carbonate). The aryl moiety of the aryloxy group is preferably a phenyl group. The substituent Z preferably represents hydrogen, or an acetyl or phenoxycarbonyl group. It has been found that yields obtained with unprotected phenols (Z=H) can sometimes be improved by derivatizing the phenolic group with one of the (protective) groups mentioned.

The Pb(IV) compound may be a Pb(IV) salt, such as $PbF_4$, $PbCl_4$, $Pb(CO_3)_2$ or $Pb(OAc)_4$, or a simple Pb(IV) oxide, such as $PbO_2$, or a salt or oxide containing Pb(IV) compounds, such as $Pb_3O_4$, or a mixture thereof. The Pb(IV) compound may conveniently be a lead oxide, carboxylate, carbonate or fluoride. Preferred Pb(IV) compounds are $PbO_2$, $Pb(OAc)_4$, $PbF_2(OAc)_2$, and, especially, $PbF_4$. As used herein Ac stands for the acetyl group $CH_3.CO$.

If the Pb(IV) compound is not present, but is replaced by a seemingly similar compound such as $MnO_2$, $Mn(OAc)_3$ or $H_2O_2$, no fluorination occurs. Although the precise mechanism of the present reaction is not understood, it is thus clear that the Pb(IV) compound is not simply functioning as an oxidizing agent.

Use of at least one mol of Pb(IV) compound per mol of compound of formula I, and at least two mol per mol when X represents a hydrogen atom, has been found to be very effective.

The compound which acts as a base towards HF, i.e. which can accept protons from HF and/or donate electrons to HF, may conveniently be a fluoride salt; a nitrogen compound of formula $NR^1R^2R^3$, wherein $R^1$, $R^2$ and $R^3$ each independently represent hydrogen or alkyl and/or $R^1$ and $R^2$ together form an alkylene group, or $R^1$, $R^2$ and $R^3$ together form an alkylidene group; a metal hydroxide or alcoholate; or water. The fluoride salt may be for example be an alkaline earth metal fluoride or, preferably, an alkali metal fluoride, especially KF. It is envisageable to use $PbF_4$ in a double function; both as the Pb(IV) compound and as the compound acting as a base towards HF. The nitrogen compound may be, for example, diethylamine, triethylamine, piperidine, pyridine, or pyrazine. Preferably it is pyridine because the system pyridine/HF is convenient to work with in the laboratory or in industry (low vapor pressure). The metal hydroxide could be an alkali metal hydroxide, optionally in aqueous solution.

Suitably the amount of HF and base should be at least sufficient to provide enough fluorine atoms as needed for the reaction with the phenol compound. Conveniently an excess is used, as this increases the conversion of the (more expensive) phenol compound.

It is not necessary to employ additional solvents or diluents or to work in multiple phase systems. However, when the phenol is more than sparingly soluble in the HF/base system, the reaction is preferably carried out in the additional presence of a liquid diluent which is substantially inert to and immiscible with hydrogen fluoride, for example a liquid aliphatic, optionally halogenated, hydrocarbon, an ether, or a mixture thereof, advantageously dichloromethane or n-pentane.

The reaction may conveniently be effected at a temperature in the range −30° to 100° C., preferably 0° to 60° C. The reaction may readily be effected at ambient temperature, e.g. about 20° C.

The starting phenols or phenol derivatives are readily available materials. The final products may be used as intermediates in the pharmaceutical or pesticide chemical industry for the synthesis of compounds which in some cases are fluoro-analogues of naturally occurring chemicals. As activated double bond containing systems they may undergo various addition reactions, e.g. Michael or Diels-Alder reactions. An especially convenient use of the compounds prepared according to the present invention is their conversion into p-fluorophenols, as described in U.K. Patent Application No. 8501918 (Applicant's ref. K 574). An especially convenient advantage is their ready separability from the starting materials (phenols): the difference in boiling points between the cyclohexadienones and the corresponding phenols is typically about 100° C., whereas the difference in boiling point between a phenol and a corresponding fluorophenol is typically only about 6° C.

The invention will be further understood from the following examples.

EXAMPLES

All yields are calculated on the intake of the phenol and given in molar percentages. All (substituted) fluorocyclohexadienones were characterized by their mass spectrum, $^1H$ magnetic resonance, $^{13}C$ magnetic resonance and $^{19}F$ magnetic resonance. The working-up procedures were the following:

Method A: GLC analysis of the crude reaction mixture using the "internal standard" method.

Method B: the organic layer was decanted from the HF-phase, extracted with an equal amount of an aqueous 5% w/w sodium carbonate solution, then with an equal amount of water and dried over magnesium sulfate. The solvent was distilled off and the product isolated from the residue (see also method C) by column chromatography.

Method C: As B, but the product was isolated from the residue by distillation.

EXAMPLE 1

Preparation of 4,4-difluorohexadienone from phenol a. 10 mmol of phenol and 20 mmol of lead dioxide were added in 15 minutes to a stirred mixture of 10 ml of 70% w/w HF in pyridine and 50 ml of dichloromethane at 35° C. The reaction mixture was then stirred for another 30 minutes.

Yield: Method A: 50%, Method B: 30%.

b. 30 mmol of phenol and 60 mmol of lead dioxide were added in 30 minutes to a mixture of 20 ml KF.9HF and 250 ml dichloromethane at 25° C. The reaction mixture was the stirred for another two hours.

Yield: Method B: 30%.

N.B. KF.9HF is a 24% w/w solution of potassium fluoride in liquid HF; molar ratio of KF:HF = 1:9.

c. 2.5 mmol of phenol in 50 ml of dichloromethane were added in liquid 15 minutes to a stirred mixutre of 5 mmol of PbF$_4$ and 3 ml of KF.9HF at 25° C. The reaction mixture was then stirred for another 60 minutes.

Yield: Method A: 65%.

d–f. The same reaction was carried out under the following conditions:

TABLE

| Ex. | Phenol, mmol | Pb compound (mmol) | | HF-base system | Diluent ml | °C. | Time h | Yield, % (Method A) |
| --- | --- | --- | --- | --- | --- | --- | --- | --- |
| 1d | 5 | Pb$_3$O$_4$ | (10) | 5 g KF.9HF | 50 CH$_2$Cl$_2$ | 25 | 16 | 41 |
| 1e | 5 | Pb(OAc)$_4$ | (10) | 5 g KF.9HF | 50 CH$_2$Cl$_2$ | 25 | 0.25 | 48 |
| 1f | 10 | PbO$_2$ | (20) | 10 ml 70% HF/pyridine | 50 n-C$_5$H$_{12}$ | 0 | 3.5 | 31 |
| 1g* | 5 | PbO$_2$ | (10) | 10 g HF | 50 CH$_2$Cl$_2$ | 5/15 | 0.5/1 | 8 |
| 1h* | 5 | PbO$_2$ | (10) | 10 g HF | — | 5/15 | 0.5/1 | 0.2 |
| 1i* | 5 | PbF$_4$ | (5) | — | 10 CH$_2$Cl$_2$ | 25 | 36 | 2 |

*not according to the invention (no base present) (1i no HF present)

EXAMPLE 2

Preparation of 2-chloro-4,4-difluorocyclohexadienone 10 mmol of 2-chlorophenol and 4.5 ml of 70% w/w HF in pyridine were added in 30 minutes to a stirred mixture of 20 mmol of lead dioxide and 50 ml of pentane at ambient temperature (20° C.). The reaction mixture was then stirred for another 30 minutes.

Yield: Method C: 25%.

EXAMPLE 3

Preparation of 4-chloro-4-fluorocyclohexadienone 10 mmol of 4-chlorophenol in 50 ml of dichloromethane were added in 30 minutes to a stirred mixture of 10 mmol of lead dioxide, 5 ml of 70% w/w HF in pyridine and 100 ml of pentane at ambient temperature (20° C.). The reaction mixture was then stirred for another 60 minutes.

Yield: Method B: 15%.

EXAMPLE 4

Preparation of 4,4-difluorohexadienone from 4-fluorophenol 10 mmol of 4-fluorophenol were added in 20 minutes to a stirred mixture of 10 mmol of lead dioxide, 1 ml 70% w/w HF in pyridine and 20 ml of dichloromethane at ambient temperature (20° C.). The reaction mixture was then stirred for another 20 minutes.

Yield: Method A: 26%.

EXAMPLE 5

Preparation of 4,4-difluoro-2-methylcyclohexadienone 5 mmol of o-cresol were added in 10 minutes to a stirred mixture of 10 mmol of lead (IV) acetate, 5 ml of KF.9HF and 100 ml of dichloromethane at ambient temperature (20° C.). The reaction mixture was then stirred for another 30 minutes.

Yield: Method B: 10%.

EXAMPLE 6

Preparation of 4-fluoro-4-methylcyclohexadienone 20 mmol of lead dioxide were added in 30 minutes to a stirred mixture of 20 mmol of p-cresol, 10 ml of 70% w/w HF in pyridine and 200 ml of dichloromethane at ambient temperature (20° C.). The reaction mixture was then stirred for another 60 minutes.

Yield: Method C: 36%.

EXAMPLE 7

Preparation of 4,4-difluoro-3-methylcyclohexadienone 10 mmol of m-cresol in 25 ml of dichloromethane were added in 40 minutes to a stirred mixture of 20 mmol of lead dioxide, 4.5 ml of 60% w/w HF in pyridine and 50 ml of dichloromethane at ambient temperature (20° C.). The reaction mixture was then stirred for another 120 minutes.

Yield: Method C: 17%.

EXAMPLE 8

Preparation of 4,4-difluorocyclohexadienone from phenylacetate 5 mmol of phenylacetate, 10 mmol of lead dioxide, 2 ml of 70% w/w HF in pyridine and 20 ml of dichloromethane were stirred for 16 hours at 25° C.

Yield: Method A: 9.2%. (conversion of phenylacetate: 43%, therefore selectivity: 21%).

We claim:

1. Process for the preparation of 4,4-di-substituted dyclohexadienones of which at least one of the 4-substituents is fluorine which process comprises reacting at a temperature in the range from about −30° to about 100° C. a compound of formula

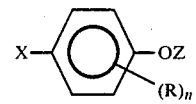

wherein X represents a hydrogen or halogen atom or an alkyl group having up to 5 carbon atoms, each R independently represents a halogen atom or a group containing up to 5 carbon atoms from alkyl, alkoxy, cyano and amino; Z represents a hydrogen atom or alkyl, acyl aryloxycarbonyl, and n is 0 to 4, with hydrogen fluoride and at least one mol of a Pb(IV) compound per mol of compound of formula I, and at least two mols of said Pb(IV) compound when X represents a hydrogen atom, and, in the presence of a compound which acts as a base towards hydrogen fluoride and wherein the amount of hydrogen fluoride and base are present in an amount at least sufficient to provide enough fluorine atoms as needed for the reaction with said compound of formula I.

2. A process according to claim 1 wherein n is 0.

3. A process according to claim 1 wherein Z represents hydrogen, acetyl or phenoxycarbonyl.

4. A process according to claim 1 wherein the Pb(IV) compound is a lead oxide, carboxylate, carbonate or fluoride.

5. A process according to claim 1 wherein the compound which acts as a base towards HF is selected from the group consisting of a fluoride salt; a nitrogen compound of formula $NR^1R^2R^3$, wherein $R^1$, $R^2$ and $R^3$ each independently represent hydrogen or alkyl and/or $R^1$ and $R^2$ together form an alkylene group, or $R^1$, $R^2$ and $R^3$ together form an alkylylidene group; a metal hydroxide or alcoholate; and water.

6. A process according to claim 5, wherein the compound which acts as a base towards HF is selected from an alkali metal fluoride and pyridine.

7. A process according to claim 1 wherein said reacting is effected in the presence of a liquid aliphatic hydrocarbon, a halogenated hydrocarbon, an ether, or a mixture thereof, as liquid diluent.

8. A process according to claim 7 wherein the liquid diluent is dichloromethane or n-pentane.

9. A process according to claim 1 wherein said reacting is carried out at a temperature in the range from about 0° to 60° C.

* * * * *